United States Patent [19]

Fiehler

[11] 4,386,003
[45] May 31, 1983

[54] BLOOD SEPARATING COMPOSITION

[75] Inventor: William R. Fiehler, St. Louis, Mo.

[73] Assignee: Sherwood Medical Industries Inc., St. Louis, Mo.

[21] Appl. No.: 303,001

[22] Filed: Sep. 17, 1981

[51] Int. Cl.³ .................. B01D 17/00; B01D 21/26
[52] U.S. Cl. ........................... 252/60; 252/315.1;
210/516; 210/789; 210/927; 106/287.13;
556/430; 422/21; 422/24
[58] Field of Search ............... 252/60, 316, 408;
210/516, 789, 927; 106/287.13; 556/430;
422/21, 24

[56] References Cited

U.S. PATENT DOCUMENTS

| 3,780,935 | 12/1973 | Lukaes et al. |
|---|---|---|
| 3,852,194 | 12/1974 | Zine, Jr. |
| 3,920,549 | 11/1975 | Gigliello et al. |
| 3,977,982 | 8/1976 | Hertl |
| 4,018,564 | 4/1977 | Wright |
| 4,049,692 | 9/1977 | Zine, Jr. |
| 4,083,784 | 4/1978 | Zine, Jr. |
| 4,101,422 | 7/1978 | Lamont et al. |
| 4,172,803 | 10/1979 | Ichikawa et al. |
| 4,180,465 | 12/1979 | Marty |
| 4,235,725 | 11/1980 | Semersky |
| 4,310,430 | 1/1982 | Ichikawa et al. ............ 252/60 |

Primary Examiner—John E. Kittle
Assistant Examiner—Hoa Van Le
Attorney, Agent, or Firm—Wood, Dalton, Phillips, Mason & Rowe

[57] ABSTRACT

A silica-silicone fluid gel, the properties of which are not significantly affected by sterilizing doses of radiation, is prepared by reaction of a silicone fluid having a narrow viscosity distribution with a filler material and a network former at or below about 120° C.

17 Claims, No Drawings

BLOOD SEPARATING COMPOSITION

BACKGROUND OF THE INVENTION

1. Field of the Invention

This invention relates to blood separating compositions and, more particularly, this invention relates to a radiation-sterilizable silica-silicone fluid gel useful for partitioning the serum and clot portions of a blood sample.

2. Brief Description of the Prior Art

The use of thixotropic gels as partitioning materials in blood collection and separating devices is well known. In such devices, a thixotropic gel having a density intermediate that of the serum and clot portions of a blood sample is disposed in a fluid collection device such that, upon centrifugation, the serum and clot portions separate with the gel disposed intermediate the portions to provide a chemical and physical barrier therebetween, thus facilitating separation of the respective portions for analysis. A preferred form of blood collection device is described in Murty U.S. Pat. No. 4,180,465, the disclosure of which is hereby incorporated by reference.

One well known type of thixotropic gel material is a silica-silicone fluid gel formed by the reaction between silicone fluid, a filler material (such as silica particles) and a thixotropic property-imparting amount of a network former. (Silicone fluids used to prepare such gels are conventionally characterized as "silicone oils", and the terms "silicone fluid" and "silicone oil", as used herein, are interchangeable.)

Hertl U.S. Pat. No. 3,977,982 and Zine, Jr. U.S. Pat. No. 4,049,692, the disclosures of which are hereby incorporated by reference, describe typical silica-silicone fluid gels and methods of preparing the same.

It is desirable, however, that a thixotropic gel used in a blood collection device be sterile in order to prevent backflow contamination to the patient. A preferred method of sterilizing a blooc collection device and gel barrier disposed therein is the use of γ-radiation, or another type of electron capture radiation. Prior silica-silicone fluid gel serum separators, however, when sterilized by radiation, harden to the point at which they are no longer functional, exhibiting viscosities in the 3,000,000 to 5,000,000 centipoise (cp) range.

Other types of thixotropic gel barrier materials which are functional after sterilization by radiation have been developed. One such material is described in Semersky U.S. Pat. No. 4,235,725, the disclosure of which is hereby incorporated by reference. The Semersky patent describes a blood collecting and separating device in which a thixotropic gel separating material comprises a mixture of liquid polybutadiene and an inorganic, inert filler which is adapted to form at rest a sealing barrier between separated blood phases. The device and gel of the Semersky patent may be subjected to sterilizing radiation to render the device and gel free of backflow contamination, allegedly without degradation of the physical properties of the gel.

While polybutadiene and other polymeric gel materials may be sterilized by exposure to radiation with only limited degradation of the gel properties, such materials tend to harden with time and thus have limited shelf lives. Silica-silicone fluid gel barrier materials, on the other hand, do not harden to a substantial degree with time, and thus exhibit extremely long shelf lives. Further, silica-silicone fluid gels tend to provide a superior chemical and physical barrier (i.e. better resistance to leakage or slippage) in a collection tube than do other polymeric barrier materials.

Thus, the need for a sterilizable silica-silicone fluid gel material useful as a blood separating composition is apparent.

SUMMARY OF THE INVENTION

It is an object of the invention to overcome one or more of the problems described above.

According to the present invention, a thixotropic silica-silicone fluid gel useful as a blood separating composition and which is sterilizable by exposure to γ or other types of radiation without a substantial adverse effect on the beneficial properties of the gel is provided. The invention contemplates, without limitation, the gel, the method of making the gel, and a fluid collecting and partitioning device incorporating the gel as a separation barrier.

According to the invention, a gel-forming reaction between a silicone fluid, a filler material and a thixotropic property-imparting amount of a network former is carried out at or below about 120° C., preferably at about 40° C., and the viscosity of the component or components of the silicone fluid are controlled within narrow limits.

Further objects and advantages will be apparent from the following detailed description taken in conjunction with the appended claims.

DETAILED DESCRIPTION OF THE INVENTION

According to the present invention, a silicone fluid (oil), a filler material and a thixotropic property-imparting amount of a network former are reacted together, preferably in a stepwise manner under evacuated conditions, at a temperature below about 120° C., and preferably below about 80° C., to form a thixotropic silica-silicone fluid gel. The gel is suitable for use as a partitioning composition between phases of a fluid, such as blood, having differing densities, and may be sterilized by exposure to sterilizing doses of γ or other electron capture types of radiation without a significant adverse effect on the properties of the gel.

As described in detail below, the respective amounts of silicone fluid, the filler material and the network former are selected such that, following the reaction, the viscosity of the gel is between about 200,000 and 450,000 cp, and preferably about 300,000 cp. Exposure of such a gel to sterilizing doses of radiation results in a final viscosity of between about 400,000 and 750,000 cp.

The specific gravity of blood serum ranges from between about 1.026 and 1.031, and the specific gravity of the clot portion of a blood sample range between about 1.092 and 1.095. Therefore, the amounts of gel forming components are selected such that the final density of the gel before and after irradiation is between about 1.03 and 1.09, and is preferably about 1.04.

As detailed below, the advantages of the invention are derived primarily by control, within relatively narrow limits, of the viscosity of each component of the silicone fluid used in the reaction, and secondarily by control of gel-forming reaction temperature, which may extend as high as 120° C. but which preferably is below about 80° C. Best results are obtained at about 40° C.

If the gel-forming reaction is carried out in a stepwise fashion, as is preferred, with pre-mixing and degassing of the silicone fluid and filler, with subsequent addition of the network former, both steps should be carried out at a temperature below about 120° C.

Prior silica-silicone fluid gel barrier materials, when sterilized by γ-radiation, exhibit a final viscosity of between about 3,000,000 and 5,000,000 cp and will not form acceptable serum separator barriers when centrifuged in most clinical centrifuges. As detailed below, the gel of the invention, when sterilized with γ-radiation, generally exhibits a viscosity below about 700,000 cp, and provides an effective physical and chemical barrier between separated serum and clot portions of a blood sample when centrifuged in any of a wide variety of centrifuges at normal operating speeds.

GEL FORMING COMPONENTS

Silicone Oil

The major gel forming component is silicone fluid (oil). A preferred type of silicone fluid is a dimethyl siloxane polymer, although others which have been found useful in prior silica-silicone fluid gels may be utilized. A preferred silicone fluid is marketed by Dow-Corning Co. (Midland, Michigan) under the designation "DC-360". Dow-Corning DC-200 silicone fluid is also suitable.

The fluid preferably has a viscosity (at 25° C.) between about 10,000 and 15,000 cs, with a fluid viscosity of about 12,500 cs being highly preferred. The fluid has a practical viscosity range of 1,000 to 100,000 cs at 25° C.

The silicone fluid preferably comprises a single stock fluid component, but a mixture of two or more blend stock fluids may be used, provided, however, that each blend stock fluid has a viscosity within ± about 15% of the desired silicone fluid viscosity.

Thus, the viscosity (and, hence, molecular weight, which is reflected by the viscosity) of the silicone fluid component of the gel should be controlled within a fairly narrow range of deviation from the desired fluid viscosity. Such narrow control of viscosity has been found to be of primary importance in obtaining the desired properties of the gel.

Filler Material

Hertl U.S. Pat. No. 3,977,982 and Zine, Jr. U.S. Pat. No. 4,049,692, both incorporated herein by reference, describe the use of various filler materials which may be used to control the final viscosity of the silicone gel. A preferred filler material is precipitated silica particles which are at least partially methylated. A preferred commercially available silica filler material is DeGussa D-17, although nonmethylated precipitated fillers (e.g. DeGussa 22-S) can be used in combination with the methylated silica, if desired.

Other inert silica fillers can be used in combination with a methylated filler. One such inert filler is marketed by Pennsylvania Glass Sand Corp. under the trademark MIN-U-SIL. If desired, water can be added in small amounts to replace a part of the filler content.

Network Former

Hertl U.S. Pat. No. 3,977,982 provides examples of various thixotropic property-imparting network formers which are useful in the practice of this invention. Such network formers stabilize the viscosity of silica-silicone fluid compositions, and have a sometimes dramatic effect in increasing the viscosity of the composition. Hence, very small amounts of network former can be used to achieve a stable, controlled viscosity in the range of about 200,000 to 450,000 cp, preferably 300,000 cp, which range is useful for blood separating applications. The appropriate amounts of the respective components are readily determined empirically. It has been observed that relatively low amounts of filler materials are required at relatively low process temperatures.

Among the network formers identified in the Hertl U.S. Pat. No. 3,977,982 and useful in this invention are water, glycerol, glycols, polyfunctional amines, and certain polysiloxane-polyoxyalkyl silicone copolymers. Such copolymers are available commercially under the trademarks DC-190, DC-192 and DC-194 from Dow-Corning Co. (Midland, Michigan). DC-190 is an especially preferred network former, and can be generally characterized as a silicone-glycol copolymer.

Reaction Conditions

Generally, the process of preparing the gel of the invention comprises the steps of mixing the filler material and the silicone fluid in proportions so as to achieve a desired specific gravity, with subsequent addition of the network former. The fluid and filler mixture is preferably degassed by mixing under evacuated conditions prior to addition of the network former, and the network former likewise mixed with the degassed components under a vacuum.

For example, roughly 15 parts (w/w) of a methylated silica filler may be added to about 100 parts of silicone fluid to achieve a specific gravity of about 1.04. The filler and silicone fluid are blended together at ambient conditions and the mixture is then degassed by mixing under evacuated conditions. A small amount (e.g. 0.01–0.02% [w/w]) of network former sufficient to bring the final viscosity of the gel to a desired value is added and blended under vacuum. For example, the mixture can be degassed at 20° C. by mixing for a period of about 30 minutes, followed by addition of approximately 0.015% (w/w) of network former, and the reaction is completed by blending under vacuum at 20° C. for about 20 minutes.

Prior practice has involved heating of the gel-forming component, during mixing, to temperatures in excess of 120° C. According to the invention, the process is performed at temperatures below 120° C., which results in considerable savings in time and expense, and which contributes to the resistance of the gel from hardening upon exposure to radiation. The reaction is preferably carried out at less than 80° C., and can be carried out at or below ambient temperatures. Excellent results are obtained at 40° C.

Thus, the selection of a fluid with a narrow viscosity distribution in combination with a process temperature below about 120° C. yields a gel which does not exhibit excessive viscosity increases upon exposure to sterilizing radiation.

Reference herein to the "reaction temperature" refers to the temperature of mixing, degassing and reaction of the silicone fluid and filler to form a premix gel, and to the temperature of mixing and reaction of the premix gel with the network former.

The following specific example will serve to illustrate the practice of the invention, but unnecessary limitations should not be inferred therefrom.

EXAMPLE 100 parts by weight of Dow-Corning DC-360 silicone fluid are blended with about 15 parts of DeGussa D-17 methylated silica filler at ambient temperature and pressure, and mixing is continued for 30 minutes after the filler powder is completely wetted by the fluid.

The resulting premix gel is then transferred to a jacketed vessel capable of maintaining a vacuum of less than 5 Torr. A helical rotor/stator bar configuration is utilized to mix the premix gel.

The premix gel is degassed by mixing at low speed while maintaining a vacuum of about 1 Torr and a gel temperature of about 40° C. The mixing is continued for a period of between 1 and 3 hours.

After the initial degassing and mixing of the premix gel is completed, about 0.01% (w/w) of Dow-Corning DC-190 network former is added to the gel and the mixing conditions (40° C., 1 Torr) are maintained for an additional 20 minutes.

As a result, a semi-transparent gel having a specific gravity of 1.04, a Brookfield viscosity (1 rpm, No. 7 spindle) of 300,000 cp and a thixotropic index of 3.2 is obtained. The gel is dispensed into the bottom of a blood collection tube into which is placed a Corvac$^R$ (Monojest Division, Sherwood Medical Industries, St. Louis, Missouri) energizer which comprises silica beads. The tube is then evacuated and stoppered.

Using sterilizing doses of $\gamma$-radiation, the gel is sterilized, and exhibits a final gel viscosity of between about 400,000 to 700,000 cp. This sterile gel is found to produce an acceptable physical and chemical barrier between the serum and clot portions of a centrifuged blood sample.

Further objects and advantages will be apparent to those skilled in the art, as obvious variations within the scope of the invention will be apparent to those skilled in the art.

I claim:

1. In a method of making a thixotropic gel for partitioning separated phases of a fluid sample, said phases having differing densities and said gel having a density intermediate those of said phases, wherein a silicone fluid, a filler material and a network former are reacted to form said gel, the improvement wherein said silicone fluid has a first viscosity and comprises a single stock fluid or a blend comprising at least two blend stock fluids, each said stock fluid having a viscosity within about ±15% of said first viscosity, said gel-forming reaction is carried out at or below about 120° C., and said gel is sterilized by exposure to a sterilizing dose of radiation.

2. The improvement of claim 1 wherein said gel-forming reaction is carried out at or below about 60° C.

3. The improvement of claim 2 wherein said first viscosity is between about 10,000 and 15,000 centistokes at 25° C.

4. The improvement of claim 3 wherein said gel-forming reaction is about 40° C. or below and said first viscosity is about 12,500 centistokes at 25° C.

5. A method of making a thixotropic gel for partitioning separated serum and clot portions of a blood sample, said method comprising the steps of:
  (a) providing a silicone fluid having a viscosity of between about 1,000 and 100,000 centistokes at 25° C., said silicone fluid comprising a single stock fluid or a blend of at least two blend stock fluids, each said stock fluid or blend stock fluid having a viscosity within about ±15% of the viscosity of said silicone fluid;
  (b) reacting said silicone fluid with a filler material and a thixotropic property-imparting amount of a network former at or below about 120° C. in such proportions as to form a gel having a viscosity between about 200,000 and 450,000 centipoise; and, sterilizing said gel by exposing said gel to a sterilizing dose of radiation.

6. The method of claim 5 wherein said radiation is $\gamma$-radiation or another form of electron capture radiation.

7. The method of claim 5 wherein said silicone fluid comprises one or more dimethyl polysiloxanes, said filler material comprises precipitated, methylated or partially methylated silica, and said network former is chosen from the group consisting of water, glycerol, glycols, polyfunctional amines, and polysiloxane-polyoxyalkylsilicone copolymers.

8. The method of claim 7 wherein the amounts of said silicone fluid, filler material and network former are selected such that said gel has a viscosity of about 300,000 centipoise and a specific gravity of about 1.04.

9. The method of claim 5 wherein said gel-forming reaction is carried out at less than about 80° C.

10. The method of claim 9 wherein said silicone fluid and said filler material are mixed under vacuum to form a first reaction mixture and said mixing is continued for a period of time sufficient to substantially completely degas said first reaction mixture, and said first reaction mixture is subsequently mixed with said network former under vacuum to form said gel.

11. The gel prepared by the method of claim 1.

12. The gel prepared by the method of claim 5.

13. A method of preparing a fluid collection and partitioning assembly comprising the steps of:
  (a) disposing the gel of claim 12 in a container having a closed end and an open end; and,
  (b) evacuating said container and closing said open end.

14. The fluid collection and partitioning assembly prepared by the method of claim 13.

15. In a substantially sterile, irradiated blood collecting and separating device comprising an enclosed container adapted to receive a blood sample and a thixotropic gel disposed therein and adapted to form a separating barrier between separated phases of said blood having differing densities, said gel having at rest a density intermediate said differing densities, the improvement wherein said gel comprises a silica-silicone fluid gel comprising the reaction product between silicone fluid having a viscosity between about 1,000 and 100,000 centistokes at 25° C., said silicone fluid comprising a single stock oil or a mixture of blend stock oils each having a viscosity within about ±15% of said silicone fluid viscosity, a filler material and a network former, and said reaction being carried out at less than about 120° C., said gel and said container are sterilized by exposure to sterilizing radiation.

16. A method of preparing a fluid collection and partitioning assembly comprising the steps of:
  (a) preparing a thixotropic gel by
    (1) providing a silicone fluid having a viscosity of between about 1,000 and 100,000 centistokes at 25° C., said silicone fluid comprising a single stock fluid or a blend of at least two blend stock fluids, each said stock fluid or blend stock fluid having a viscosity within about ±15% of the viscosity of said silicone fluid; and (2) reacting said silicone fluid with a filler material and a thixotropic property-imparting amount of a network former at or below about 120° C. in such proportions as to form a gel having a viscosity between about 200,000 and 450,000 centipoise;

(b) disposing the gel of step (a) in a container having a closed end and an open end;

(c) evacuating said container and closing said open end; and, (d) exposing said tube and said gel to a sterilizing dose of electron capture-type radiation for a time sufficient to sterilize said gel and said tube.

17. The fluid collection and partitioning assembly prepared by the method of claim 16.

* * * * *